(12) United States Patent
Thomas et al.

(10) Patent No.: US 6,192,740 B1
(45) Date of Patent: *Feb. 27, 2001

(54) METHOD AND APPARATUS FOR DETECTING PARTICLES IN A FLOW

(75) Inventors: Victor Frederick Thomas; Michael Rigby, both of Huntingdon (GB)

(73) Assignee: PCME Limited, Cambridgeshire (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/522,390

(22) PCT Filed: Mar. 31, 1994

(86) PCT No.: PCT/GB94/00711

§ 371 Date: Nov. 22, 1995

§ 102(e) Date: Nov. 22, 1995

(87) PCT Pub. No.: WO94/23281

PCT Pub. Date: Oct. 13, 1994

(30) Foreign Application Priority Data

Apr. 6, 1993 (GB) .................................... 9307123

(51) Int. Cl.[7] .................................................. G01N 25/00
(52) U.S. Cl. ........................................ 73/28.01; 324/454
(58) Field of Search ............................. 73/28.01, 861.04, 73/861.08; 324/452, 454

(56) References Cited

U.S. PATENT DOCUMENTS 3,753,102 * 8/1973 Beck ..................................... 324/453
3,813,939   6/1974 Head .
3,944,354   3/1976 Benwood et al. .

(List continued on next page.)

FOREIGN PATENT DOCUMENTS

| 1195960 | 7/1965 | (DE) . |
| 2121542 * | 12/1983 | (DE) .............................. G01N/27/60 |
| 0110802A3 | 6/1984 | (EP) . |
| 0144193A2 | 6/1985 | (EP) . |
| 62003621A | 1/1987 | (EP) . |
| 62003622A | 1/1987 | (EP) . |
| 0256845A2 | 2/1988 | (EP) . |
| 0256845 * | 2/1988 | (EP) .............................. G01N/27/62 |
| 0386665 * | 9/1990 | (EP) .............................. G01N/15/02 |
| 7402814 | 8/1974 | (FR) . |
| 1485750 * | 9/1977 | (GB) .............................. G01N/15/02 |
| 1578157 | 11/1980 | (GB) . |
| 2121542 | 12/1983 | (GB) . |
| 2166874A | 5/1986 | (GB) . |
| 2266772 * | 11/1993 | (GB) .............................. G01F/1/64 |
| WO 86 02453 | 4/1986 | (WO) . |
| WO 86 02454 | 4/1986 | (WO) . |

OTHER PUBLICATIONS

Rossner et al, Measurement of Micrometer Particles by Means of Induced Charges, Oct. 1989, IEEE 3613521.*

Primary Examiner—Hezron Williams
Assistant Examiner—Jay L. Politzer
(74) Attorney, Agent, or Firm—Pitney, Hardin, Kipp & Szuch, LLP

(57) ABSTRACT

An apparatus for detecting particles in a flow comprises a probe 1 positioned so that it projects into the flow and is charged triboelectrically by the particles in the flow. An electric circuit is coupled to the probe 1 and includes evaluating means for monitoring a signal from the probe 1 and for providing an output in dependence on the signal generated by the triboelectric charging of the probe 1. The part of the probe 1 that projects into the particle flow comprises an electrically conducting core covered with an insulating layer 2 which insulates the core from the particle flow.

34 Claims, 3 Drawing Sheets

U.S. PATENT DOCUMENTS

| | | |
|---|---|---|
| 4,179,934 | 12/1979 | Svarovsky . |
| 4,512,200 * | 4/1985 | Ghering et al. .................. 73/861.04 |
| 4,592,240 * | 6/1986 | McHale et al. .................. 324/453 X |
| 4,594,901 * | 6/1986 | Norman ............................ 73/861.04 |
| 4,607,228 | 8/1986 | Reif . |
| 4,631,482 | 12/1986 | Newton et al. . |
| 4,714,890 * | 12/1987 | Dechene et al. ..................... 324/454 |
| 4,904,944 * | 2/1990 | Dechene et al. ..................... 324/454 |
| 5,022,274 | 6/1991 | Klinzing et al. . |
| 5,054,325 | 10/1991 | Dechene et al. . |
| 5,095,275 | 3/1992 | Dechene et al. . |
| 5,214,386 * | 5/1993 | Singer et al. ........................ 324/452 |
| 5,287,061 | 2/1994 | Dechene et al. . |
| 5,396,806 | 3/1995 | Dechene et al. . |
| 5,563,516 * | 10/1996 | Babbitt et al. ....................... 324/454 |
| 5,591,895 * | 1/1997 | Rigby ................................. 73/28.01 |

\* cited by examiner

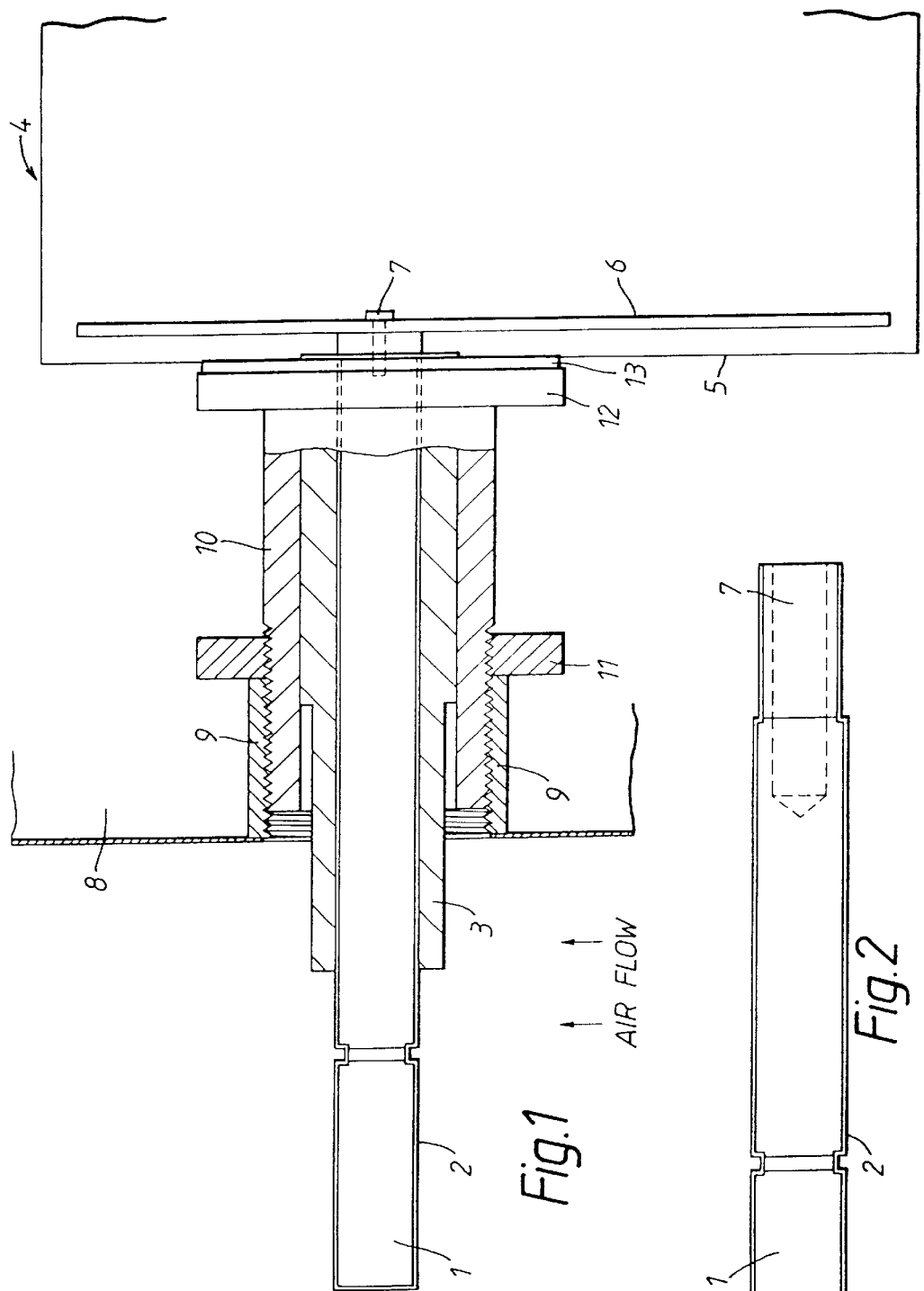

METHOD AND APPARATUS FOR DETECTING PARTICLES IN A FLOW

This invention relates to a method and apparatus for monitoring particles.

The invention particularly relates to an arrangement in which a probe projecting into a flow of particles is charged triboelectrically by flowing particles colliding with the probe.

WO 86/02454 describes an apparatus for monitoring particles in a gas flow through a conduit. A metal probe is installed in a flow of gas containing solid particles and the probe is coupled to an electric circuit containing processing means. The probe is charged triboelectrically by the particles colliding with the probe and the resulting current in the circuit is processed to give an output that gives a measure of the flow rate of the particles.

U.S. Pat. No. 5,054,325 shows an apparatus for measurement of fluid flows with suspended solid particles, using a triboelectric probe embedded in the wall of the conduit through which the fluid flows, where the fluid flow is a liquid or gas.

U.S. Pat. No. 5,591,895 the content of which is incorporated herein by reference also describes an arrangement for monitoring particles in a gas flow. An electrically conducting rod is mounted in a stack and is coupled to a processing circuit. The rod is charged triboelectrically by the particles in the gas flow and the signal generated in the circuit is evaluated to give an output giving an indication of the particle flow. The rod is insulated at the point where it is mounted in the stack wall to prevent currents being transmitted to and from the stack wall, but of course the insulating material does not extend over the whole outer surface of the conducting rod.

In the arrangements described above, a probe extends into the fluid flow and obstructs the flow of the particles. It has been found that if the probe is mounted in a duct wall or the like, particles can build up in the region between the electrically conducting probe and the duct wall and, especially in damp conditions, form an electrically conducting path between the probe and the duct wall.

As a result, the charge transferred to the probe by the particles in the flow can pass through the built-up material and through the duct wall to earth. Thus the output of the processing circuit may not give an accurate measure of the particle flow.

In addition, small currents that exist in the duct wall can be transmitted via the probe into the processing circuit connected to the probe. The magnitude of the currents generated by the triboelectrical charging of the probe in the circuit may be of the same order as those that exist in the duct wall and so the output of the circuit may not give an accurate measure of the particle flow.

A further problem is that the metal probe and the duct wall may begin to operate as a battery, introducing more undesirable currents into the processing circuit, again giving an inaccurate measure of the particle flow.

It is an object of the invention to provide an improved method and apparatus for detecting particles in a flow that avoids or mitigates the above problems and gives a reliable indication of the particle flow.

Accordingly, the present invention provides a method of detecting particles in a flow in which a probe is positioned so that it projects into the flow of particles and is charged triboelectrically by the particles in the flow and a signal from the probe is evaluated to provide an indication of the particle flow, characterised in that the part of the probe that projects into the particle flow comprises an electrically conducting core covered with an insulating layer which insulates the core from the particle flow.

Advantageously the A.C. component of the signal is evaluated to provide an indication of the particle flow. Although the A.c. component of the signal generated in the circuit by triboelectrical charging of the probe is small when compared with the D.C. component, it has been found that the A.C. component of the signal gives a more accurate reflection of the particle flow than the absolute value of the signal. It is believed that factors such as humidity, electrical charges already on the particles and a build-up of particles on the probe all affect the absolute value of the current without affecting the alternating component of the current as much. We have found furthermore that the combination of providing an insulated probe and evaluating the A.C. component is especially advantageous because the use of A.C. is especially suited to the case where the probe is insulated.

Preferably the alternating component of the signal from the probe is filtered to limit the frequency to below about 5 Hz. The frequency may be limited to below 2 Hz, preferably about 1.5 Hz. By eliminating higher frequencies the risk of spurious signals derived from mechanical vibration of the probe is substantially reduced since the resonant frequency of such vibration is likely to be substantially higher than 5 Hz.

Preferably the alternating component of the signal from the probe is filtered to limit the frequency of the signal to above about 0.1 Hz, preferably about 0.15 Hz. By eliminating lower frequencies the risk of spurious signals derived from transient temperature-generated voltages is substantially reduced.

Preferably the alternating component of the signal from the probe is amplified in a plurality of stages. In that case low frequencies, which may be those below 0.15 Hz, are preferably attenuated at the first stage of amplification.

The particles may be suspended in a fluid flow. The fluid flow may be either a gas or a non-electrically conducting liquid and the particles may be either liquid or solid particles.

The flow may be a gas flow through a stack with suspended particles that are emitted through the stack.

The flow may be through a duct having a probe mounted in the duct.

The present invention also provides an apparatus for detecting particles in a flow comprising a probe to be positioned so that it projects into the flow to be charged triboelectrically by the particles in the flow, and an electric circuit coupled to the probe having evaluating means for monitoring a signal from the probe and for providing an output in dependence on the signal generated by the triboelectric charging of the probe, characterised in that the part of the probe to project into the particle flow comprises an electrically conducting core covered with an insulating layer which insulates the core from the particle flow.

Advantageously, the electric circuit comprises evaluating means for monitoring the A.C. component of the signal from the probe. The probe may be in the form of a rod. The rod probe may be of circular cross-section.

It is, of course, entirely unconventional to use an insulated probe to monitor triboelectrical charging but we have found the use of such a probe to be surprisingly effective in the present invention, especially in terms of overcoming the problems referred to above.

In the prior art particle monitoring arrangements, a conducting rod probe is mounted in a duct wall with the electrically conducting surface of the probe exposed to the gas flow and the probe is coupled to a processing circuit. It is believed that a current is generated by the rod probe in the following ways:

(1) When a particle collides with the probe there is a "rubbing" of the particle against the probe leading to direct triboelectric charging.

(2) Particles in the flow may become charged by collisions with other particles. When a charged particle collides with the conducting probe, the particle gives up some or all of its charge to the probe. The particle may be charged positively or negatively and the current generated will vary accordingly.

(3) A charged particle in the flow passing the probe may, even though it does not touch the probe, induce a charge in the probe which causes a current to flow.

In the case of the present invention it is believed that currents are usually generated as a result of all three of the effects described above although precisely what happens is not fully understood. It is believed that the probe and evaluating means of the present invention may be likened in electrical terms to the same evaluating means coupled to a non-insulated probe connected in series with a capacitor.

Advantageously,the size and composition of the particles in the flow does not vary and the flow is monitored in order to detect variations in the mass flow rate. Given that the size of the particles and their composition does not vary, the measurement of mass flow rate can alternatively be regarded as a measurement of the flow rate in terms of the number of particles per unit time.

Usually it will be desired to provide a quantitative indication of the mass flow rate but for some applications it may be adequate simply to provide an indication of whether or not the mass flow rate measured is above or below some threshold level. An alarm may be sounded if the mass flow rate is above the threshold level.

The invention can be used to monitor a flow of solid particles alone or to monitor solid or liquid particles suspended in a gas or liquid flow. The invention can be used to provide a continuous measurement of the mass flow rate of the suspended particles. The invention has many applications in industrial plants using particle collection and dry solids handling processes. It may be used, for example, to monitor the performance of a filter. A particularly advantageous and important use for the invention is the measurement of the emission of particles classified as pollutants through a stack to the atmosphere. The invention can also be used in a manufacturing process where it is necessary to monitor and control the addition or recovery of particulate matter. For example, the invention may be used in a system where particles are suspended in a gas stream, as in a pneumatic conveying system.

An apparatus and method for monitoring flow of particles in accordance with the invention will now be described by way of example only with reference to the accompanying drawings, in which:

FIG. 1 is a sectional view of the sensing head of the dust flow monitoring apparatus mounted in the wall of a stack through which dust particles in a flow of air are emitted;

FIG. 2 is a sectional view of the insulated probe assembly of the sensing head;

Figure 3:
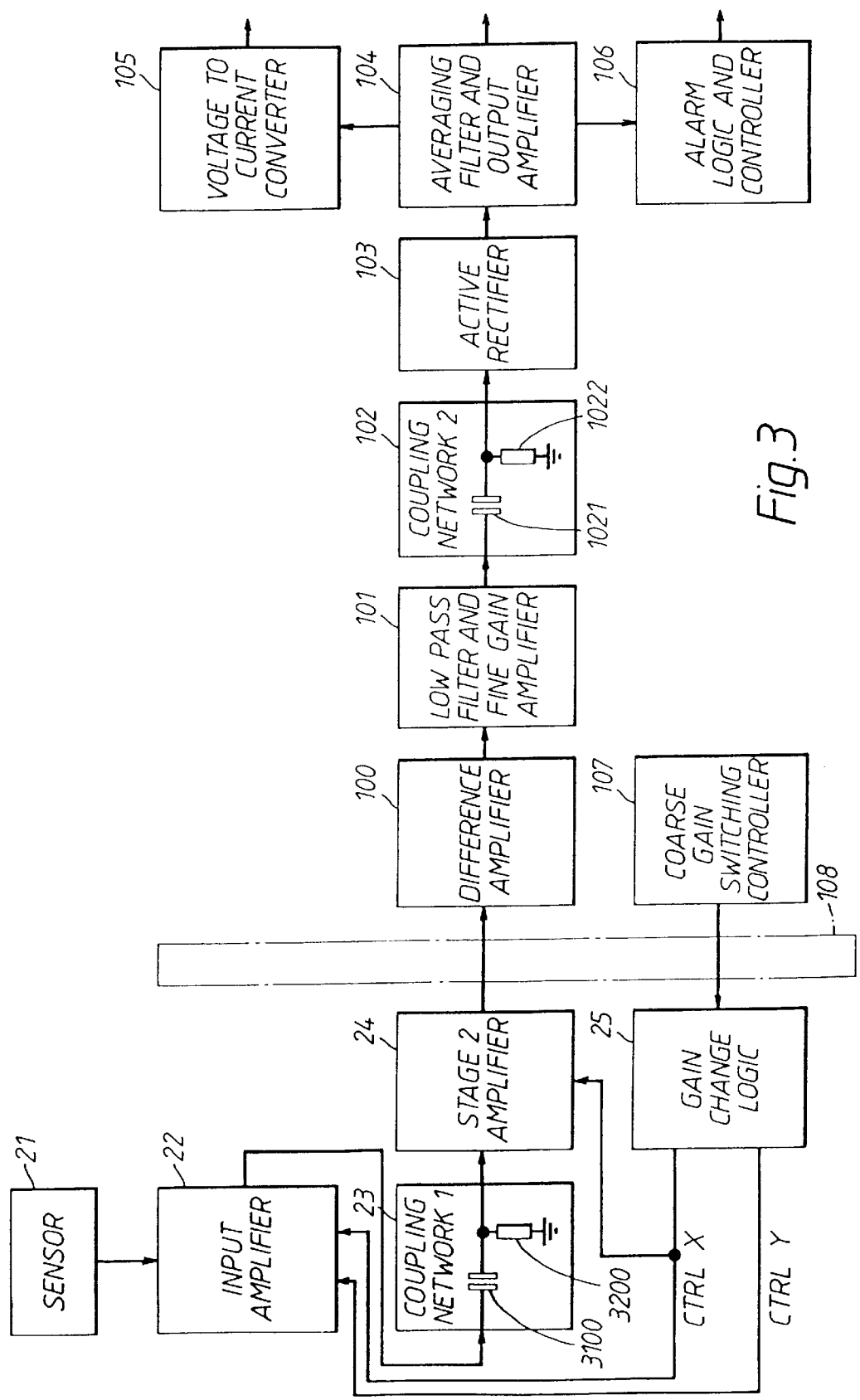
FIG. 3 is a block diagram representation of the electrical system of the dust flow monitoring system.

With reference to FIG. 1 of the accompanying drawings, the sensing head of the dust flow monitoring apparatus generally comprises a metal probe 1 with a layer of insulating material 2 on the outer surface, an insulated support member 3, made of PTFE, and an electronic sensor unit 4 comprising a waterproof box 5 containing an electronic circuit board 6.

With reference to FIG. 2, the probe assembly is a metal rod 1 of circular cross-section with a diameter of 16 mm and 150 mm long made of stainless steel and coated on the outer surface, using known techniques, with a nylon powder coating 2. The stainless steel rod is coated with the insulating material over the entire surface except the end of the rod that is to be connected to the circuit board. The thickness of the insulating layer is 5 $\mu$m.

FIG. 1 shows the probe and a sensor unit 4 making up the sensing head fitted in the stack wall 8.

The electronic sensor unit 4 comprises an aluminium cover 5 containing a circuit board 6 carrying signal evaluating means and is connected to the metal probe by means of a connection screw 7. The connection screw 7 passes through the circuit board 6 and connects it to the metal probe 1.

The sensing head is mounted in the stack wall 8 in the following way. A position for mounting the sensing head 11 in the stack is chosen where the gas flow is reasonably linear, for example, as shown, in a straight section of the stack. An internally screw threaded sleeve 9 is then welded into the stack at the chosen position. An outer metal sleeve 10 having an external screw thread matching the internal thread on the coupling is fitted around the insulating support member 3. The sensing head is then inserted into the stack wall and screwed into place so that the probe extends into the gas flow. A lock nut 11 secures the sensing head in the stack wall. A second lock nut 12 acts on a sealing gasket 13 that is placed around the end of the probe between the metal sleeve 10 and the sensing unit 4.

As shown in FIG. 1 the probe projects into the shaft of the stack in a direction transverse to the direction of flow of air through the stack. Particles in the air flow collide with the probe and triboelectric charging takes place. A signal is thus produced in the circuit coupled to the probe.

FIG. 3 shows a block diagram illustrating the electronic circuitry of the dust monitoring apparatus. Our co-pending application no. GB 90.09407 describes in full detail the circuitry used to evaluate a current generated by a metal probe in an apparatus for detecting particles in a gas flow. The same circuitry is used in the dust monitoring apparatus described here. However, as described above, the signal generated in the circuit by the insulated probe is different from the signal generated in the circuit when it is coupled to a non-insulated metal probe. The electronic circuit board in the sensor shown in FIG. 1 contains the input amplifier 22, the first coupling network 23, the second stage amplifier 24 and the gain-change logic circuit 25. The rest of the electrical system is "control room" equipment and is located at a position remote from the sensing head.

The signal is processed in the same way as is described in our co-pending application GB 2 266 772. Briefly, referring to FIG. 3, the current supplied by the probe is amplified and subjected to bandwidth shaping. The signal is also passed through coupling networks 23,102 containing capacitors that block the d.c. and very low frequency signals in the circuit. Finally, the signal is passed to an averaging filter and output amplifier 104 that provides a long-term average of the signals, reducing the random signal variations which particle flow provides. The output signal from the output amplifier is passed to a voltage-to-current converter 105 for driving a pen-recorder or the like.

Also, a signal from the averaging filter and output amplifier 104 is applied to the alarm logic and controller 106 which is set to trigger when a set level is exceeded. There is also an arrangement for setting the alarm logic and controller to trigger when the applied signal falls below a set threshold.

Because the outer layer of the probe is electrically insulated, even if there is a build-up of particles in the region between the probe and the stack wall, there is no electrically conducting path between the stack wall and the processing circuit.

In that way the reading given by the dust monitoring apparatus is a more accurate measure of the particle flow.

Figure 4:
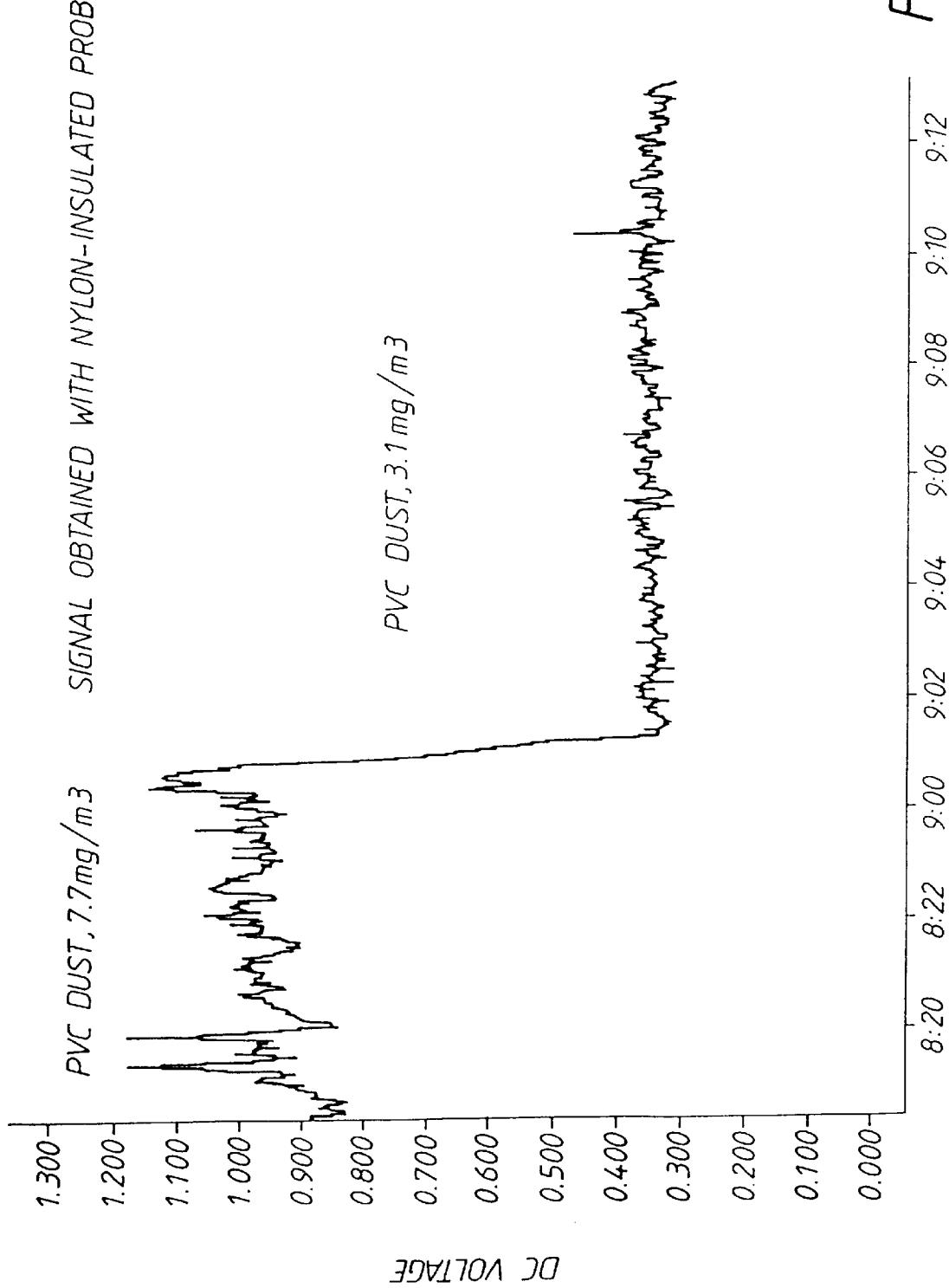
FIG. 4 is a graph showing the d.c. voltage outputs from the monitoring system monitoring an air flow to which polyvinylchloride (PVC) dust particles have been added at two different constant rates.

FIG. 4 shows the results, in the form of voltage in volts plotted against time in minutes, of a test carried out to measure the result of monitoring particles using the monitoring apparatus described above at given densities in an air flow through a duct. In the test, PVC particles of substantially constant size of 200 microns were added to air flowing at a rate of 18.5 m/s through a duct of circular cross-section. The particles were first added at a substantially constant rate of the order of 7.7 mg/m3 and the output from the evaluating means was measured. Similarly, PVC particles were later added at a substantially constant rate of approximately 3.1 mg/m3 and the output was again measured. FIG. 4 shows that the reading obtained by the evaluating means in each case is substantially constant and approximately proportional to the density of the particles.

The invention is not limited to use in a stack as described above. As will be clear to a person skilled in the art, the invention can be used to monitor any flow of particles, whether flowing under the action of gravity, or suspended in a gas or non-electrically conducting liquid. Other types of insulating material would be suitable for use on the probe. For example, the insulating layer could be nylon, polytetrafluoroethene (PTFE), ceramic or any plastic, whether thermoplastic or thermosetting, and it could be in the form of a coating or a sleeve. Although the circuit described above coupled to the probe evaluates the A.C. component of the signal generated by the probe, the insulated probe is also suitable for use with a circuit where the D.C. component, or both the A.C. and the D.C. component, of a signal generated by the probe is evaluated to give an output reading that is a measure of the particle flow.

What is claimed is:

1. A method of detecting particles flowing along a emitted through the stack in which a probe is positioned so that it projects into the flow of particles and is charged by the particles in the flow characterized in that the part of the probe that projects into the particle flow comprises an electrically conducting core covered with an insulating layer which insulates the core from the particle flow and the A.C. component of a signal from the probe is evaluated to provide an indication of the particle flow.

2. Method as claimed in claim 1 in which the particles are suspended in a fluid flow and the probe is charged triboelectrically by the particles in the fluid flow.

3. A method as claimed in claim 1 in which the fluid is a gas and the particles are liquid or solid particles suspended in the gas.

4. A method as claimed in claim 1 in which the A.C. component of the signal from the probe is filtered to exclude high frequency components of the signal.

5. A method as claimed in claim 4 in which the A.C. component of the signal from the probe is filtered to limit the frequency to below about 5 Hz.

6. A method as claimed in claim 1 or claim 4 in which the A.C. component of the signal is filtered to exclude low frequency components of the signal.

7. A method as claimed in claim 6 in which the A.C. component of the signal is filtered to limit the frequency to above about 0.1 Hz.

8. Apparatus for detecting particles flowing along a stack and emitted through the stack comprising a probe to be positioned so that it projects into the flow to be charged by the particles in the flow, and an electric circuit coupled to the probe characterized in that the part of the probe to project into the particle flow comprises an electrically conducting core covered with an insulating layer which insulates the core from the particle flow, and the electric circuit has evaluating means for monitoring an A.C. component of the signal from the probe for providing an output in dependence on the signal generated by the triboelectric charging of the probe.

9. Apparatus as claimed in claim 8 characterized in that the probe is in the form of a rod.

10. Apparatus as claimed in claim 9 characterized in that the rod is of circular cross-section.

11. Apparatus as claimed in claim 8 in which the electric circuit comprises filter means for filtering out high frequency components of the signal.

12. Apparatus as claimed in claim 11 in which the filter means are for limiting the frequency of the A.C. component of the signal to below about 5 Hz.

13. Apparatus as claimed in claim 8 or claim 11 in which the electric circuit comprises filter means for filtering out low frequency components of the signal.

14. Apparatus as claimed in claim 13 in which the filter means are for limiting the frequency of the A.C. component to above about 0.1 Hz.

15. A method of detecting particles flowing along a stack and emitted through the stack in which a probe is positioned so that it projects into the flow of particles and is charged by the particles in the flow characterized in that the part of the probe that projects into the particle flow comprises an electrically conducting core covered with an insulating layer which insulates the core from the particle flow, the signal from the probe is filtered to block the D.C. signal and the A.C. signal is evaluated to provide an indication of the particle flow.

16. Apparatus for detecting particles flowing along a stack and emitted through the stack comprising a probe to be positioned so that it projects into the flow to be charged by the particles in the flow, and an electric circuit coupled to the probe characterized in that the part of the probe to project into the particle flow comprises an electrically conducting core covered with an insulating layer which insulates the core from the particle flow, and the electric circuit has filter means for blocking the D.C. signal from the probe an evaluating means for monitoring the filtered A.C. signal for providing an output in dependence on the signal generated by the triboelectric charging of the probe.

17. A method of detecting particles flowing along a stack and emitted through the stack in which a probe is positioned so that it projects into the flow of particles and is charged by the particles in the flow characterized in that the part of the probe that projects into the particle flow comprises an electrically conducting core covered with an insulating layer which insulates the core from the particle flow, that the signal from the probe is filtered to limit the signal to an A.C. signal of frequency above about 0.1 $H_z$ and the A.C. signal is evaluated to provide an indication of the particle flow.

18. Apparatus for detecting particles flowing along a stack and emitted through the stack comprising a probe to be positioned so that it projects into the flow to be charged by the particles in the flow, and an electric circuit coupled to the probe characterized in that the part of the probe to project into the particle flow comprises an electrically conducting core covered with an insulating layer which insulates the core from the particle flow, and the electric circuit has filter means for limiting the signal from the probe to an A.C. signal of frequency above about 0.1 $H_z$ and evaluating means for monitoring the filtered A.C. signal for providing an output in dependence on the signal generated by the triboelectric charging of the probe.

19. A method of detecting particles flowing along a stack and emitted through the stack in which a probe is positioned so that it projects into the flow of particles and is charged by the particles in the flow characterised in that the part of the probe that projects into the particle flow comprises an electrically conducting core covered with an insulating layer which insulates the core from the particle flow and a signal from the probe is filtered to exclude frequency components below about 0.1 Hz and above about 5 Hz and is evaluated to provide an indication of the particle flow.

20. A method of detecting particles flowing along a stack and emitted through the stack in which a probe is positioned so that it projects into the flow of particles and is charged by the particles in the flow characterised in that the part of the probe that projects into the particle flow comprises an electrically conducting core covered with an insulating layer which insulates the core from the particle flow, the insulating layer being substantially thinner than the conducting core, and a signal from the probe is evaluated to provide an indication of particle flow.

21. A method as claimed in claim 20, in which the signal for the probe is filtered to exclude frequency components below about 0.1 Hz.

22. A method as claimed in claim 20, in which the signal for the probe is a current signal which is converted into a voltage signal, said voltage signal being passed through signal processing means which block the DC component of the voltage signal to generate a processed voltage signal and said processed voltage signal being subsequently evaluated to provide an indication of the particle flow.

23. A method of detecting particles flowing along a stack and emitted through the stack in which a probe is positioned so that it projects into the flow of particles and is charged by the particles in the flow characterised in that the part of the probe that projects into the particle flow comprises an electrically conducting core covered with an insulating layer which insulates the core from the particle flow and the probe generates a current signal which is converted into a voltage signal, said voltage signal being passed through signal processing means which block the DC component of the voltage signal to generate a processed voltage signal, and, said processed voltage signal being subsequently evaluated to provide an indication of the particle flow.

24. A method as claimed in claim 23, in which said processed voltage signal excludes frequency components below about 0.1 Hz.

25. Apparatus for detecting particles suspended in a gas flow flowing along a gas flow path emitted through a sack, the apparatus comprising:

a probe projecting into the gas flow path for detecting particles in the gas flow along the stack, a wall defining a boundary of the gas flow path, the probe comprising an electrically conducting core and a covering layer, the covering layer being electrically insulating and serving to block conduction of a DC current from the surface of the probe through the insulating layer to the electrically conducting core of the probe, the probe being fixed in the wall with the electrically conducting core electrically insulated from the wall, and an electric circuit connected to the electrically conducting core of the probe for evaluating the signal from the core of the probe for providing an output in dependence on the signal generated by the charging of the probe.

26. Apparatus as claimed in claim 25, in which the probe is in the form of a rod.

27. Apparatus as claimed in claim 26, in which the rod is of circular cross-section.

28. Apparatus as claimed in claim 25, in which the electric circuit comprises filter means for filtering out high frequency components of the signal.

29. Apparatus as claimed in claim 28, in which the filter means are for limiting the frequency the AC component of the signal to below about 5 Hz.

30. Apparatus as claimed in claim 25, in which the electric circuit comprises filter means for iltering out low frequency components of the signal.

31. Apparatus as claimed in claim 30, in which the filter means are for limiting the frequency of the AC component to about 0.1 Hz.

32. A method for detecting particles flowing in a gas flow along a stack and emitted through the stack in which a probe including a portion which comprises an electrically conducting core covered by an insulating layer which insulates the core from particle flow is positioned so that said portion projects into the flow of particles in the stack and is charged triboelectrically by particles in the flow and the quantities of electrical charges transferred to the probe are evaluated to provide an indication of the particle flow in the gas flow, wherein, in order to reduce the effect of variations in gas flow related variables other than those relating to particle flow, an alternating component in the signal caused by the triboelectrical charging of the probe is monitored, the alternating component of the signal from the probe is filtered to exclude high frequency components of the signal and the magnitude of the residual alternating component is itself used to give an indication of the particle flow through the stack.

33. The method according to claim 32 in which the alternating component of the signal from the probe is filtered to limit the frequency to about 0.10 Hz.

34. The method according to claim 32 in which said insulating layer is substantially thinner than said conducting core.

* * * * *